United States Patent
Kawada et al.

(10) Patent No.: US 7,666,145 B2
(45) Date of Patent: Feb. 23, 2010

(54) PULSE WAVE TRANSMISSION DETECTION SYSTEM

(75) Inventors: Reiji Kawada, Yamaguchi (JP); Syoichi Takano, Saitama (JP)

(73) Assignee: BML, Inc., Tokyo (JP)

( * ) Notice: Subject to any disclaimer, the term of this patent is extended or adjusted under 35 U.S.C. 154(b) by 690 days.

(21) Appl. No.: 10/519,710

(22) PCT Filed: Jul. 3, 2003

(86) PCT No.: PCT/JP03/08477

§ 371 (c)(1),
(2), (4) Date: Oct. 12, 2005

(87) PCT Pub. No.: WO2004/004556

PCT Pub. Date: Jan. 15, 2004

(65) Prior Publication Data

US 2006/0122524 A1 Jun. 8, 2006

(30) Foreign Application Priority Data

Jul. 3, 2002 (JP) .............................. 2002-194553

(51) Int. Cl.
*A61B 5/02* (2006.01)
*G06K 9/00* (2006.01)

(52) U.S. Cl. .................. 600/500; 600/483; 382/128

(58) Field of Classification Search ................. 600/485, 600/500–503, 513, 504, 561; 382/128
See application file for complete search history.

(56) References Cited

U.S. PATENT DOCUMENTS

| 6,390,989 B1 * | 5/2002 | Denninghoff | 600/561 |
| 6,621,917 B1 * | 9/2003 | Vilser | 382/128 |
| 6,999,812 B2 * | 2/2006 | Kawada et al. | 600/479 |

* cited by examiner

*Primary Examiner*—Charles A Marmor, II
*Assistant Examiner*—Christian Y Jang
(74) *Attorney, Agent, or Firm*—Sughrue Mion, PLLC

(57) ABSTRACT

Provided is a pulse wave propagation detection system including an electrocardiographic signal detection unit, and an eyeground image detection unit for detecting an eyeground image in synchronization with an electrocardiographic signal detected through the detection unit, which system further includes a correlation unit for correlating a change in the diameter of an eyeground vein—which diameter is measured, at the optic papilla, by use of an eyeground image synchronized with an arbitrary electrocardiographic signal—with the state of pulse wave propagation through an intracerebral blood vessel or with the state of sclerosis of a capillary artery.

20 Claims, 5 Drawing Sheets

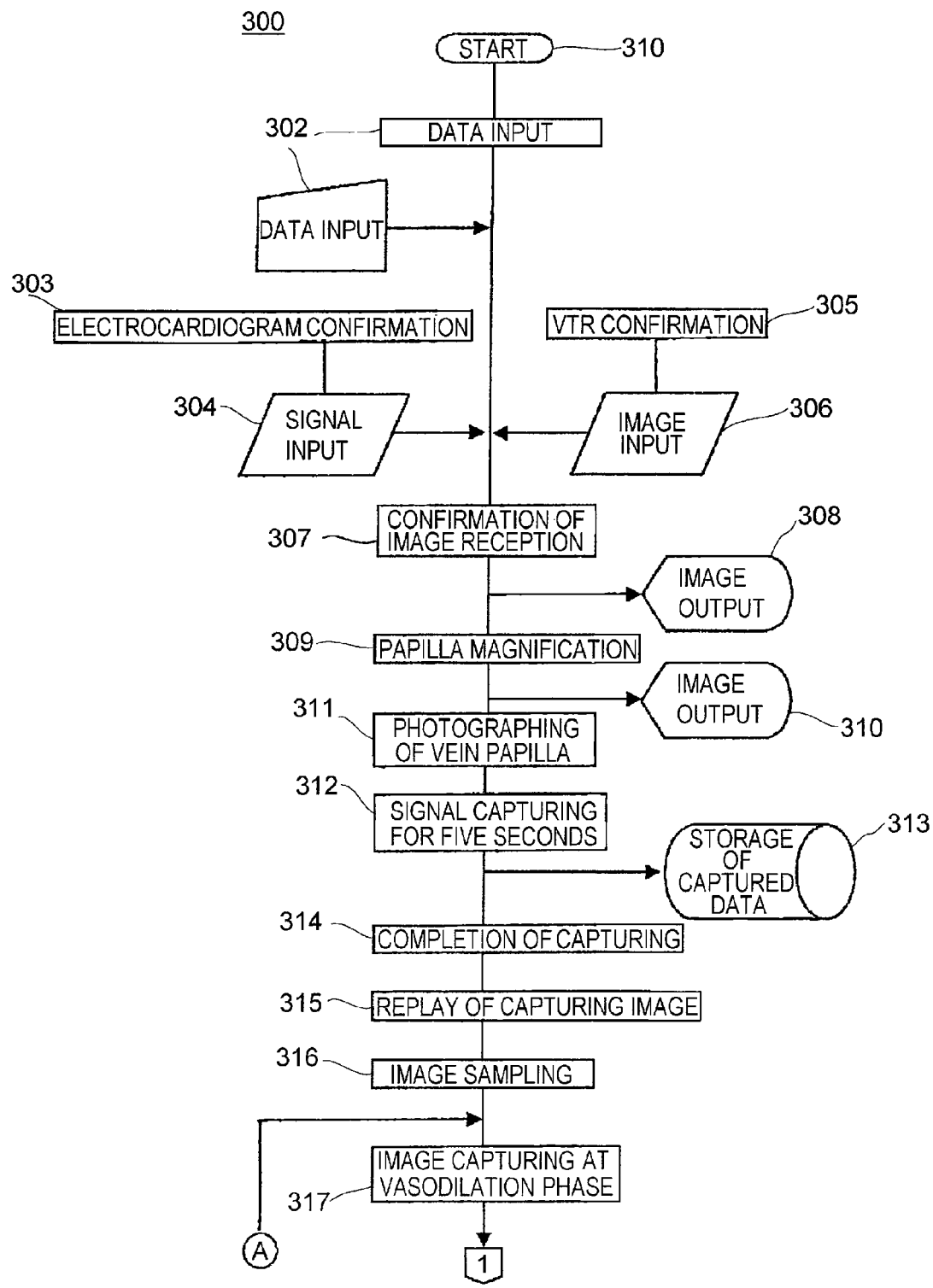

PULSE WAVE TRANSMISSION DETECTION SYSTEM

TECHNICAL FIELD

The present invention relates to a pulse wave propagation detection system.

BACKGROUND ART

Monitoring loss or considerable reduction of pulsation in capillary blood vessels is considered to be important for the maintenance of health conditions.

(1) Approach to Hypotension

In general, the term "hypotension" refers to the case where maximum blood pressure is 110 to 100 mmHg or less. Hypotension is classified into the following types: "essential hypotension," with which no causative disease is found; "orthostatic hypotension"; i.e., a fall in blood pressure that occurs when a person suddenly rises from a recumbent position or stands up, which may cause, for example, dizziness or light-headedness; and "symptomatic hypotension," which is caused by some disease (e.g., diabetes).

Less attention has been drawn to hypotension as compared with hypertension, which is also a pathological condition related to blood pressure. However, hypotension is known to cause various symptoms, including dizziness, light-headedness, and general malaise. Particularly, in the elderly, there is concern about accidents caused by light-headedness, or progress of dementia, which could occur as a result of reduction of pulse wave propagation through intracerebral blood vessels. Therefore, in the elderly, further attention must be paid to reduction of pulse wave propagation through intracerebral blood vessels.

(2) Approach to Sclerosis of Capillary Artery

As has been reported, pulse wave velocity (PWV) in large- or medium-sized arteries can be used as an index for evaluating the degree of atherosclerosis or coronary artery risk. Specifically, since the wall of a large- or medium-sized artery of a healthy human exhibits elasticity as in the case of the wall of a rubber tube, a pulse wave; i.e., a pulsation of a blood vessel caused by blood pumped out of the heart (propagation of the pulse wave through the blood vessel indicates the presence of blood flow in the blood vessel), is absorbed by the artery wall, and thus PWV tends to be lowered. In contrast, when sclerosis progresses in a large- or medium-sized artery, the wall of the artery becomes hard, and thus a pulse wave is not readily absorbed by the artery wall, and PWV tends to be increased. Thus, PWV in large- or medium-sized arteries has increasingly become of interest as an index for evaluating health conditions.

PWV in a large- or medium-sized artery can be measured by use of, for example, an apparatus for detecting the blood pressure of extremities.

PROBLEMS TO BE SOLVED BY THE INVENTION (1) Approach to Hypotension

In the elderly, etc., when arteriosclerosis progresses, the blood pressure tends to increase in order to secure blood flow in the body. That is, higher blood pressure is required for maintaining blood circulation conditions as those in the past. In view of the pulse wave propagation necessary for maintaining blood flow in the brain, as arteriosclerosis progresses, higher blood pressure is required for maintaining blood circulation conditions as those in the past. Needless to say, the difference in blood pressure between individuals should be taken into consideration.

Meanwhile, in order to prevent cerebral circulatory diseases (e.g., cerebral stroke) induced by hypertension and arteriosclerosis, undoubtedly, administration of a hypotensive drug is required. However, an excessive drop in blood pressure induces hypotension, leading to excessive reduction of pulse wave propagation through an intracerebral blood vessel, resulting in excessive suppression of blood flow in the brain. Therefore, the blood pressure must be maintained at a certain level such that blood flow in the brain is not excessively suppressed.

Such a blood pressure level must be determined on the basis of whether or not blood flow is secured in the brain. However, the blood pressure level should not be determined univocally, since the level differs between individuals.

Conventionally, blood flow in the brain has been measured by means of a method employing, for example, positron CT capable of evaluating the metabolic state of the brain, or xenon CT capable of evaluating the state of cerebral blood flow. However, such a method employs a radioactive substance, and thus is less versatile from the viewpoint of, for example, restriction on use of a radioactive substance, or requirement of high cost.

In view of the foregoing, a first object of the present invention is to provide means for conveniently and accurately identifying the state of blood flow in the brain.

(2) Approach to Sclerosis of Capillary Artery

Data on pulse wave propagation through a capillary artery are considered very important for monitoring the state of the interior of the capillary artery (in particular, the state of sclerosis of the capillary artery).

That is, when the state of blood flow in a capillary artery is specified, the period of onset of cerebrovascular or cardiovascular disorders can be accurately predicted. Therefore, demand has arisen for means for detecting such a blood flow state. However, unlike the case of a pulse wave propagated through a large- or medium-sized artery, a pulse wave propagated through a capillary artery is very weak, and thus the capillary artery pulse wave is difficult to detect by the aforementioned blood pressure detection apparatus.

The conditions of pulse wave of capillary arteries are directly reflected on capillary veins via tissue vessels. A capillary artery has a three-layer structure formed of tunica intima, tunica media, and tunica adventitia, and exhibits high elasticity, whereas a capillary vein has a two-layer structure formed of tunica intima and tunica adventitia, and does not include tunica media. Therefore, a capillary vein has a thin wall, exhibits low elasticity, and directly reflects pulsation (a pulse wave); i.e., a capillary vein is suitable for comprehensive monitoring of pulse waves. However, it is very difficult to detect even pulsation (a pulse wave) in a capillary vein present in the vicinity of the body surface, not to mention in a capillary vein present inside the body.

In view of the foregoing, a second object of the present invention is to provide means for conveniently and reliably identifying the state of sclerosis of a capillary artery, which should be taken seriously for the maintenance of health conditions.

DISCLOSURE OF THE INVENTION

The present inventors have focused attention on that eyeground veins [as used herein, the term "eyeground vein" refers to an eyeground capillary vein (retinal capillary vein)] are connected directly to the cerebral circulatory system, and thus the eyeground veins enable direct monitoring of the state of blood flow in the brain, and have conducted studies on means for conveniently and accurately measuring blood flow in the brain.

As a result, the present inventors have found that pulse wave propagation through an intracerebral blood vessel, which is an index for directly evaluating the state of blood flow in the brain, can be conveniently and accurately detected on the basis of a change in the diameter of an eyeground vein, which change occurs as a result of the pulsation of the vein. As described above, a pulse wave corresponds to a pulsation of a blood vessel caused by blood pumped out of the heart (propagation of the pulse wave through the blood vessel indicates the presence of blood flow in the blood vessel).

Specifically, firstly, the present inventors have found that when the state in which the pulsation of an eyeground vein is lost (i.e., no change in the diameter of the eyeground vein occurs) is regarded as the state in which the Windkessel phenomenon is lost, and no pulse wave propagation occurs in an intracerebral blood vessel; i.e., blood flow stagnates in the brain, the state of blood flow in the brain can be accurately understood.

Secondly, the present inventors have focused attention on that a pulse wave is propagated from an eyeground artery (as used herein the term "eyeground artery" refers to an eyeground capillary artery) via retinal cell tissues to an eyeground vein, and that the amplitude of the pulse wave propagated from the eyeground artery is almost accurately reflected on the eyeground vein, and the pulsation of the vein (i.e., a change in the diameter of the vein) is readily determined by use of a fundus camera. As a result, the present inventors have found that sclerosis of an capillary artery can be detected on the basis of the change in the eyeground vein diameter.

Furthermore, the present inventors have found that, in order to accurately and conveniently determine a change in the diameter of an eyeground vein, which change occurs as a result of the pulsation of the vein, desirably, the eyeground vein diameter is measured in synchronization with an electrocardiographic signal corresponding to the Windkessel phenomenon; specifically, the eyeground vein diameter is measured by means of the eyeground image detection system for detecting arteriosclerosis (WO 01/30235 A1) which has been provided by the present inventors. The present invention has been accomplished on the basis of these findings.

The eyeground image detection system includes electrocardiographic signal detection means, electrocardiographic signal identification means for identifying an electrocardiographic signal detected through the detection means, and eyeground image detection means for detecting an eyeground image in synchronization with the thus-identified electrocardiographic signal. This system can accurately measure the diameter of an eyeground vein by use of a photograph of the eyeground, irrespective of the time lag between a diastolic phase and a systolic phase of the heart, which is caused by the Windkessel phenomenon.

According to a first aspect of the present invention, there is provided a pulse wave propagation detection system comprising electrocardiographic signal detection means, and eyeground image detection means for detecting an eyeground image in synchronization with an electrocardiographic signal detected through the detection means (hereinafter, a system including these detection means may be referred to as a "fundamental system"), which detects pulse wave propagation through an intracerebral blood vessel on the basis of a change in the diameter of an eyeground vein (a retinal vein), the diameter being measured by use of an eyeground image synchronized with an arbitrary electrocardiographic signal (hereinafter, the pulse wave propagation detection system may be referred to as "the present detection system 1").

According to a second aspect of the present invention, there is provided a pulse wave propagation detection system comprising the fundamental system, which detects the state of sclerosis of a capillary artery by detecting pulse wave propagation through the artery on the basis of a change in the diameter of an eyeground vein, the diameter being measured by use of an eyeground image synchronized with an arbitrary electrocardiographic signal (hereinafter, the pulse wave propagation detection system may be referred to as "the present detection system 2," and the present detection systems 1 and 2 may be collectively referred to as "the present detection system").

No particular limitations are imposed on the electrocardiographic signal detection means, so long as the means can detect an electrocardiographic signal accurately. For example, the detection means may be means in which an electrode sensor containing a piezoelectric element is mounted on the chest or another site of a subject, to thereby detect the output electrocardiographic signal. Typically, the mechanism of a conventional electrocardiograph may be employed as the electrocardiographic signal detection means.

The electrocardiographic signal may be selected arbitrarily. Specifically, the electrocardiographic signal may be any signal selected from established patterns of an electrocardiogram. Preferably, the electrocardiographic signal can be identified as an established wave pattern of an electrocardiogram, excluding the case of employment of the below-described means for synchronizing the electrocardiographic signal with an eyeground image on a computer display. Specifically, the electrocardiographic signal may be any wave pattern selected from among a P wave, a Q wave, an R wave, an S wave, and a T wave. However, preferably and practically, an R wave, which is a pattern signal detected when blood is fed from the heart to the entire body, or a T wave, which corresponds to recovery of ventricular activation, is employed.

No particular limitations are imposed on the lead for obtaining an electrocardiographic signal from a subject, and the lead may be selected from, for example, "standardized 12 lead ECG." Preferably, a suitable lead is selected in accordance with the type of the above-selected specific electrocardiographic signal. That is, a lead that enables detection of the specific electrocardiographic signal as easily as possible is preferably selected. For example, when an R wave is selected as an electrocardiographic pattern signal, lead II, lead I, or lead $_aV_L$, in which the difference in electric potential between the left and right hands of a subject is measured, is preferably employed.

The present detection system may include, as an optional element, "electrocardiographic signal identification means," which is employed in the case where, for example, an electrocardiographic signal must be subjected to any treatment before an eyeground image is synchronized with the electrocardiographic signal. The electrocardiographic signal identification means identifies the electrocardiographic signals detected by the electrocardiographic signal detection means, and from the thus-identified signals, a specific pattern signal is extracted as an electric signal. The thus-extracted specific pattern signal is transmitted to the eyeground image detection means. If desired, the specific pattern signal may be subjected to, for example, amplification processing, which is preferably associated with the eyeground image detection means. As the electrocardiographic signal identification means, there may be employed, for example, an output terminal of a conventional electrocardiograph, which detects a specific electrocardiographic signal (e.g., an R wave or a T wave), and transmits the signal to the outside.

As described above, the eyeground image detection means detects an eyeground image in synchronization with the electrocardiographic signal identified by the electrocardiographic signal identification means.

Within the context of the present invention, the term "synchronize" refers to the case where, with respect to an electrocardiographic signal, the eyeground image detection means is caused to respond at a predetermined timing. For example, when an R wave, which is a typical wave pattern, is selected as an electrocardiographic signal, the eyeground image detection means is operated at an arbitrary point of the R wave. No particular limitations are imposed on the manner of determining the timing at which the eyeground image detection means is operated, so long as the cycle of the timing is equal to or shorter than that between a point at which an electrocardiographic signal rises and a point at which the same signal rises again (e.g., a timing between a point at which an R wave rises and a point at which the next R wave rises). Thus, when an eyeground image is detected in synchronization with an electrocardiographic signal, accurate data on eyeground blood vessels can be obtained; specifically, accurate data on the diameter of an eyeground vein, which are necessary for detecting pulse wave propagation through an intracerebral blood vessel in the present invention, can be obtained. As described above, when an eyeground photograph that has been taken at an arbitrary time is employed, accurate measurement of the diameters of eyeground veins—which vary with diastole and systole of the heart due to the Windkessel phenomenon—is difficult. However, when an eyeground image is detected in synchronization with an electrocardiographic signal, an image of eyeground veins can be captured at a certain timing with respect to pulsation, resulting in accurate measurement of the diameters of eyeground veins.

Typical examples of the eyeground image detection means include a camera having a mechanism capable of photographing the eyeground (specifically, a so-called fundus camera, which may be of analog type or digital type). In this case, the camera is operated such that releasing of the shutter for capturing the eyeground image is synchronized with emergence of a specific pattern of an electrocardiographic signal. Meanwhile, detecting an eyeground image by use of a digital video camera capable of continuously capturing an eyeground image as digital image data is suitable for the below-described synchronization of the eyeground image with an electrocardiographic signal by use of a computer.

Needless to say, when an eyeground image is captured by use of a camera or a digital video camera, the light source to be employed can be visible rays, which have conventionally been employed. However, the light source may be appropriate ultraviolet or infrared rays. As used herein, the expression "appropriate rays" refers to rays having a wavelength and an intensity which are suitable for capturing an image of eyeground veins and which do not adversely affect the human body (the same shall apply hereinafter). When appropriate ultraviolet or infrared rays are employed, a subject can be prevented from dazzling, and a clear image of eyeground veins can be obtained. In the case where such ultraviolet or infrared rays are employed as a light source, photographing by use of a camera or a digital video camera requires a photosensitive element and a film which exhibit suitable photosensitivity to such rays.

The present detection system 1 enables an image of eyeground veins to be captured at a certain timing with respect to pulsation. When the state of pulse wave propagation through an intracerebral blood vessel of a subject is analyzed by correlating data obtained from the eyeground vein image with pulse wave propagation through the intracerebral blood vessel, the state of blood flow in the brain can be understood. Meanwhile, when the state of pulse wave propagation through an eyeground vein is analyzed by correlating the data obtained from the eyeground vein image with sclerosis of a capillary artery by means of the present detection system 2, the state of sclerosis of the capillary artery can be detected.

As described above, a specific index for establishing such correlation in the present detection system is a change in the diameter of an eyeground vein.

Specifically, in the present detection system, when a change in the eyeground vein diameter in association with an electrocardiographic signal is confirmed, a pulse wave is propagated through an intracerebral blood vessel in accordance with pulsation of the heart; i.e., blood flow is maintained in the brain, whereas when no change in the eyeground vein diameter is confirmed, no pulse wave propagation occurs in an intracerebral blood vessel; i.e., blood flow stagnates in the brain. Meanwhile, when a change in the eyeground vein diameter in association with an electrocardiographic signal is large, conceivably, sufficient blood flow is maintained in the brain (the present detection system 1).

In the present detection system 2, in the case where a time-course change in the eyeground vein diameter in association with an electrocardiographic signal is measured, when a pulse wave diagram corresponding to the time-course change is similar to a pulse wave diagram showing dilation and constriction of a large- or medium-sized artery in relation to pulses generated immediately after pulsation of the heart of a healthy human, the pulse wave is understood to have been propagated through a healthy capillary artery exhibiting high elasticity; i.e., the capillary artery is not sclerosed. In contrast, when discontinuity is observed in a portion or the entirety of the pulse wave diagram corresponding to the time-course change in the eyeground vein diameter (specifically, when an inflection point—which is not observed in a pulse wave diagram showing dilation and constriction of a large- or medium-sized artery of a healthy human—is observed in the pulse wave diagram corresponding to the time-course change, or when a point corresponding to a sharp increase or decrease in the rate of change in the eyeground vein diameter is observed in the pulse wave diagram), the pulse wave is understood to have been propagated through a capillary artery in which sclerosis or stenosis progresses; i.e., the capillary artery is sclerosed.

In an analysis method employing the present detection system 2, the state of sclerosis of a capillary artery can be determined on the basis of a differential curve of a curve of a pulse wave diagram corresponding to data on an eyeground vein. For example, in the case where the pattern of a differential curve of a curve of a pulse wave diagram corresponding to data on an eyeground vein of a subject is compared with the pattern of a differential curve of a curve of a pulse wave diagram showing dilation and constriction of a large- or medium-sized artery of a healthy human (e.g., comparison between these differential curves in terms of the shape of peaks present in the positive and negative regions of the curves), when these differential curve patterns coincide with each other, a capillary artery of the subject is determined to maintain a healthy state, whereas when these differential curve patterns do not coincide with each other, there is a likelihood that abnormal conditions (e.g., sclerosis) occur in a capillary artery of the subject. Thus, the state of sclerosis of a capillary artery can be determined on the basis of a differential curve of a curve of a pulse wave diagram corresponding to data on a capillary vein. Particularly when peaks of a differential curve of a curve of a pulse wave diagram corresponding to data on an eyeground vein of a subject are sharper than those of a differential curve of a curve of a pulse wave diagram showing dilation and constriction of a large- or medium-sized artery of a healthy human, there is a high likelihood that abnormal conditions (e.g., sclerosis) occur in a capillary artery of the subject.

When the range of change in the diameter of an eyeground vein of a subject is lower as compared with the case of a healthy human having the same blood pressure as the subject, as described above, conceivably, sufficient blood flow is not maintained in the brain of the subject, and pulsation tends not to occur in a capillary artery as a result of sclerosis of the artery.

In the present detection system 1, a specific mode of the change in the diameter of an eyeground vein, which can be used as an index for detecting pulse wave propagation through an intracerebral blood vessel, is the absolute amount of change in the eyeground vein diameter; i.e., the difference between the maximum eyeground vein diameter and the minimum eyeground vein diameter. The maximum eyeground vein diameter can be determined by measuring, at a target site, the diameter of an eyeground vein on the basis of an eyeground image captured in synchronization with an R wave (i.e., an electrocardiographic signal indicating a diastolic phase of a blood vessel) at a point in time of the end of the R wave; i.e., at a timing at which, statistically, eyeground veins are maximally dilated. Meanwhile, the minimum eyeground vein diameter can be determined by measuring, at a target site, the diameter of an eyeground vein on the basis of an eyeground image captured in synchronization with a T wave (i.e., an electrocardiographic signal indicating a systolic phase of a blood vessel) at a point in time of the end of the T wave; i.e., at a timing at which, statistically, eyeground veins are maximally constricted.

In the present detection system 1, another specific mode of the change in the diameter of an eyeground vein, which can be used as an index for detecting pulse wave propagation through an intracerebral blood vessel, is the rate of change in the eyeground vein diameter. The rate of change in the eyeground vein diameter can be determined by obtaining the difference between eyeground vein diameters measured at a target site on the basis of eyeground images captured in synchronization with two different electrocardiographic signals serving as target signals. Typically, the rate of change in the eyeground vein diameter is a value representing the difference between eyeground vein diameters measured at a target site on the basis of eyeground images captured in synchronization with the end of an R wave (i.e., an electrocardiographic signal indicating a diastolic phase of a blood vessel) and with the end of a T wave (i.e., an electrocardiographic signal indicating a systolic phase of a blood vessel).

Effectively, the amount of change in the eyeground vein diameter on the basis of unit time may be obtained as the rate of change in the eyeground vein diameter. In the case where the eyeground vein diameter is represented by "y," the initial measurement time of the eyeground vein diameter is represented by "t," and the time between the initial measurement time and the next measurement time of the eyeground vein diameter is represented by "$\Delta t$," when the "$\Delta t$" is reduced such that the function of the eyeground vein diameter "y" and the time "t"; i.e., y=f(t), can be approximated to the linear function f(t)=at+b (wherein b represents the minimum eyeground vein diameter; the same shall apply hereinafter), the absolute value of the gradient "a" of the linear function f(t) =at+b may be employed as the rate of change in the eyeground vein diameter. In this case, when the absolute value of the gradient "a" is zero, the pulsation of an eyeground vein is not observed, and pulse wave propagation is found to be suppressed in an intracerebral blood vessel; i.e., blood flow stagnates in the brain, whereas when the absolute value of the gradient "a" is larger than zero, pulse wave propagation is observed in an intracerebral blood vessel; i.e., blood flow is found to be secured in the brain, and "run off" by virtue of the pulsation of the blood vessel is observed.

As described above, in the present detection system 2, a time-course change in the eyeground vein diameter; for example, the profile of the entirety of a pulse wave diagram corresponding to the change in the eyeground vein diameter, is used as an index for detecting sclerosis of a capillary artery. The pulse wave diagram can be formed through the following procedure: eyeground vein diameters "$y_m$" are measured (sampled) at a plurality of points in time "$t_m$," and plots corresponding to the thus-measured values are connected so as to form a time-course continuous curve. If desired, a differential curve may be formed, through known means, from the thus-obtained pulse wave diagram corresponding to the change in the eyeground vein diameter.

In the present detection system, the time "t" may be determined arbitrarily. However, the amount of change in the eyeground vein diameter on the basis of unit time varies in a certain cycle of blood vessel pulsation of a single subject, due to the Windkessel phenomenon. Therefore, in order to accurately correlate the change in the eyeground vein diameter with the state of blood flow in the brain or with the state of sclerosis of a capillary artery, the time "t" is specified by use of an electrocardiographic signal with which an eyeground image has been synchronized; the eyeground image is caused to depend on the electrocardiographic signal, serving as a standard of the cycle of pulsation; and error in measurement of the amount of change in the eyeground vein diameter within the cycle of pulsation, which error is attributed to the difference in diameter between eyeground veins, is eliminated. Therefore, although the time "t" may be determined arbitrarily, the time "t" must be determined in accordance with the electrocardiographic signal with which the eyeground image has been synchronized. Preferably and practically, the time "t" is determined on the basis of an R wave or a T wave, which is a typical wave pattern of an electrocardiographic signal. The aforementioned difference between eyeground vein diameters corresponding to the end of an R wave and the end of a T wave is calculated when the "t" is determined to be a point in time at the end of the R or T wave, and the "$\Delta t$" is determined to be the time from the end of the R wave to the end of the T wave or the time from the end of the T wave to the end of the next R wave.

In the present detection system 2, in the case where eyeground vein diameters are measured (sampled) at a plurality points in time, when, for example, an eyeground image is captured by use of a digital video camera, preferably, the eyeground vein diameters are measured by use of all the frames of the thus-captured successive images, or a predetermined number of frames selected from the images.

In the present detection system 2, in the case where a camera is employed for capturing an eyeground image, when, for example, capturing of an eyeground image is performed a plurality of times in synchronization with an electrocardiographic signal at different capturing start times "$t_0$," the diameter of an eyeground vein can be measured in a time-course manner. Specifically, for example, the point in time at which the first eyeground image capturing step is started is determined to be the time of end of an R wave (hereinafter the end time may be referred to as "$t_0$"), and the first eyeground image capturing step is performed a plurality of times corresponding to a predetermined number of electrocardiographic cycles. Subsequently, the point in time at which the second eyeground image capturing step is started is determined to be a point in time ($t_1$) 10 milliseconds after $t_0$, and the second eyeground image capturing step is performed a plurality of times corresponding to a predetermined number of electrocardiographic cycles. Thereafter, the point in time at which the third eyeground image capturing step is started is determined to be a point in time 10 milliseconds after $t_1$, and the third capturing step is performed a plurality of times corresponding to a predetermined number of electrocardiographic cycles. The fourth and subsequent eyeground image capturing steps are performed in a manner similar to that described above. Finally, the diameter data of an eyeground vein can be obtained by use of the eyeground images which have been captured at the R wave end time and at intervals of 10 milliseconds after the R wave end time. In this case, eyeground image capturing may be performed in the following manner: the point in time at which the first eyeground image capturing step is performed at an initial electrocardiographic cycle is determined to be the time of end of a specific electrocardiographic signal (e.g., an R wave), and the second and subsequent eyeground image capturing steps are performed at the subsequent electrocardiographic cycles at certain intervals (e.g., at intervals of 100 milliseconds) without synchronization with the electrocardiographic signal. Alternatively, the point in time at which the second eyeground image capturing step is performed at an initial electrocardiographic cycle may be determined to be the time 10 milliseconds after the R wave end time, and the third and later eyeground image capturing steps are performed at intervals of 100 milliseconds. Thus, when capturing of an eyeground image is performed a plurality of times such that only the first capturing step is synchronized with an electrocardiographic signal, the diameter data of an eyeground veins can be obtained at different points in time.

Data on the eyeground vein diameter as obtained at numerous points in time, which are necessary for implementing the present detection system 2, are plotted in a time-course manner, to thereby form a desired pulse wave diagram in relation to the eyeground vein. Specifically, this pulse wave diagram is formed through the following procedure. A known mathematical processing is performed; for example, data on the above-measured eyeground vein diameter are plotted in a time-course manner, and a continuous curve is formed on the basis of a regression equation. Through this procedure, discontinuous points as obtained from the data on the above-measured eyeground vein diameter can be connected to form a deduced continuous curve. In this case, in order to enhance the reliability of the pulse wave diagram, preferably, the number of samples (data) is increased as much as possible. This pulse wave diagram can be formed by use of currently commercially available software. For example, a time-course line graph is formed by use of general-purpose spreadsheet software on the basis of the data on the eyeground vein diameter, and the resultant line graph is subjected to any mathematical processing, to thereby easily form a pulse wave diagram.

In the present detection system, the target site at which the eyeground vein diameter is measured is preferably the optic papilla, at which eyeground veins pulsate most strongly. That is, in the present detection system, the target site at which the eyeground vein diameter is measured preferably contains at least the optic papilla.

The eyeground vein diameter may be measured for individual target sites through direct visual observation of an eyeground image obtained by use of the eyeground image detection means. Eyeground vein diameter measuring means capable of measuring the eyeground vein diameter for individual target sites may be provided in the aforementioned eyeground image detection means, and the measuring process may be automated. Examples of the eyeground vein diameter measuring means include software in which means for measuring the diameter of an eyeground vein at a target site on the basis of the aforementioned eyeground image data—the data having been input by use of a scanner and converted into electronic data—is programmed. When the aforementioned eyeground image data are processed by use of such software, the eyeground vein diameter can be measured conveniently and reliably.

In the most preferred mode of the present detection system, detection of an eyeground image is performed by use of software which can provide an eyeground image synchronized with an electrocardiographic signal by extracting, on a computer display, a stationary eyeground image synchronized with an arbitrary electrocardiographic signal from a motion eyeground image (successive image) (hereinafter the software may be referred to as "the present software").

In this mode, a motion eyeground image captured by use of a digital video (DV) camera serving as the eyeground image detection means is input, as digital data, into a computer via, for example, a DV terminal (media converter is also available) and a DV capture card such as IEEE1394 card, EZDV (product of Canopus Co., Ltd.), DVRapter (product of Canopus Co., Ltd.), or DVRex (product of Canopus Co., Ltd.), with an electrocardiographic signal converted into a digital signal by use of, for example, an analog/digital (A/D) converter being input into the computer. Subsequently, the input motion eyeground image data and the input electrocardiographic signal data are combined in parallel so as to synchronize the eyeground image data with the electrocardiographic signal data in the same frame, thereby yielding digital synchronization data of the motion eyeground image data and the electrocardiographic signal. The digital synchronization data may be subjected to compression, so long as data required for implementing the present detection system are not lost. Coding such as compression may be performed by means of a coding format such as MPEG or MP3.

The thus-obtained digital synchronization data may be stored in, for example, a magnetic tape, a magnetic disk, CD-ROM, CD-R, CD-RW, MO, DVD-R, DVD+R, DVD-RW, DVD+RW, or DVD-ROM.

As described above, measurement of the diameter of an eyeground vein on the basis of the thus-obtained digital synchronization data is performed by extracting a stationary image; i.e., digital data per frame, from the synchronization data. Specifically, the amount of change in the eyeground vein diameter on the basis of unit time can be calculated by use of stationary eyeground image data extracted from motion eyeground image data at a point in time "t" corresponding to an arbitrary electrocardiographic signal, and stationary eyeground image data extracted from the motion eyeground image data at another point in time "t+$\Delta$t." As described above, the time "t" is preferably determined in accordance with an electrocardiographic signal which has been synchronized with a motion eyeground image.

When the eyeground vein diameter at the time "t" is represented by "$r_1$," and the eyeground vein diameter at the time "t+$\Delta$t" is represented by "$r_2$," the amount of change in the eyeground vein diameter on the basis of unit time "$\Delta$t"; i.e., $\Delta r$, can be calculated by use of the following formula:

$$\Delta r = |r_1 - r_2|/\Delta t$$

When stationary image data are extracted from digital synchronization data of motion eyeground image data and electrocardiographic signal data while the motion eyeground image and the electrocardiogram are displayed on display means (e.g., a computer display) of a computer terminal, extraction operation can be visualized. Such visualization of extraction operation is preferred. Therefore, the present software preferably includes a program for executing visualization means employing such display means of a computer terminal.

When the present software is employed for implementing the present detection system 1, the software preferably includes a program for executing means for calculating the change in the eyeground vein diameter on the basis of an eyeground image synchronized with an arbitrary electrocardiographic signal; specifically, a program for executing means for calculating the amount of change in the eyeground vein diameter on the basis of unit time by obtaining data on the eyeground vein diameter at a target site by use of eyeground images synchronized with different electrocardiographic signals.

When the present software is employed for implementing the present detection system 1, the software preferably includes a program for executing means for correlating the change in the eyeground vein diameter with pulse wave propagation through an intracerebral blood vessel; specifically, correlating the above-calculated amount of change in the eyeground vein diameter with pulse wave propagation through an intracerebral blood vessel, thereby detecting the pulse wave propagation. In this correlation, for example, when no change in the eyeground vein diameter is observed, no pulse wave propagation occurs in an intracerebral blood vessel; i.e., blood circulation in the brain is not observed, whereas when the amount of change in the eyeground vein diameter is lower than a normal level, pulse wave propagation is suppressed in an intracerebral blood vessel; i.e., blood flow in the brain is reduced.

Meanwhile, the present software is employed for implementing the present detection system 2, the algorithm of the software preferably includes a mathematical processing step for forming a time-course pulse wave diagram from a plurality of data on the measured diameter of an eyeground vein of a subject; a step for determining whether or not a capillary artery of the subject is sclerosed by employment of the entire profile of the thus-formed pulse wave diagram (in a preferred mode, the entire profile of the pulse wave diagram is compared with that of a pulse wave diagram corresponding to a large- or medium-sized artery of a healthy human), or by extracting, from the thus-formed pulse wave diagram, distinguishing portions which would arise when the capillary artery is sclerosed; and a step for determining whether or not the capillary artery is sclerosed on the basis of characteristic features of the positive and negative regions of a differential curve of a curve of the pulse wave diagram (e.g., the shape of peaks present in the positive and negative regions of the differential curve).

In the present software, a desired algorithm can be formed by use of a typical computer programming language.

Examples of the computer programming language which may be employed include low-level languages such as a machine language and an assembly language; high-level languages such as Fortran, ALGOL, COBOL, C, BASIC, PL/I, Pascal, LISP, Prolog, APL, Ada, Smalltalk, C++, and Java (registered trademark); fourth generation languages; and end user languages. If desired, special purpose languages may be employed.

The present invention also provides a computer program comprising an algorithm for executing the present software. The present invention also provides an electronic medium containing the present software, which is executed by means of the computer program.

No particular limitations are imposed on the electronic medium in which the present software can be stored. Examples of the electronic medium which may be employed include a magnetic tape, a magnetic disk, CD-ROM, CD-R, CD-RW, MO, DVD-R, DVD+R, DVD-RW, DVD+RW, and DVD-ROM.

As described above, according to the present detection system, when a change in the diameter of an eyeground vein is obtained, pulse wave propagation through an intracerebral blood vessel (i.e., the state of blood flow in the brain) can be determined conveniently and accurately.

When the present detection system is implemented, in many cases, obtaining data on the blood pressure (the maximum blood pressure and/or the minimum blood pressure) of a subject is important.

As described above, in general, the case where the maximum blood pressure is 110 to 100 mmHg or less is defined as "hypotension." However, this definition could not be applied to patients (in particular, elderly patients) with advanced arteriosclerosis. A patient with advanced arteriosclerosis requires a high blood pressure for securing intracerebral pulse wave propagation (i.e., blood flow in the brain) comparable to that in the case of a healthy human. Therefore, even when the patient is seemingly non-hypotensive or hypertensive, the blood pressure of the patient would not be sufficient for securing blood flow in the brain. In such a case, when discretion is exerted in determining proper blood pressure range, and a hypotensive drug is administered to the patient on a routine regimen, the blood pressure of the patient may become excessively low, and sufficient blood flow in the brain may fail to be secured, raising risks; for example, induction of cerebral ischemia as a result of loss of the difference in blood flow pressure between capillary blood vessels of cerebral cortex or perforating branch (the present detection system 1).

Therefore, the present detection system 1 is advantageous in that the system can provide an indication for appropriate blood pressure control in accordance with individuals.

In the present detection system 2, particularly when the range of change in the diameter of an eyeground vein of a subject is employed as a factor for determining sclerosis of a capillary artery of the subject, since the blood pressure of the subject affects the range of change in the eyeground vein diameter, a critical point is that sclerosis of an eyeground artery is detected at different blood pressure levels (between the maximum blood pressure and the minimum blood pressure) of the subject with reference to standard data on the range of change in the eyeground vein diameter as determined on healthy humans.

BRIEF DESCRIPTION OF THE DRAWINGS

FIGS. 3A through 3C shows an example of a flowchart on the basis of the algorithm of the present software.

MODES FOR CARRYING OUT THE INVENTION

Embodiments of the present invention will next be described with reference to the appended drawings.

Figure 1:
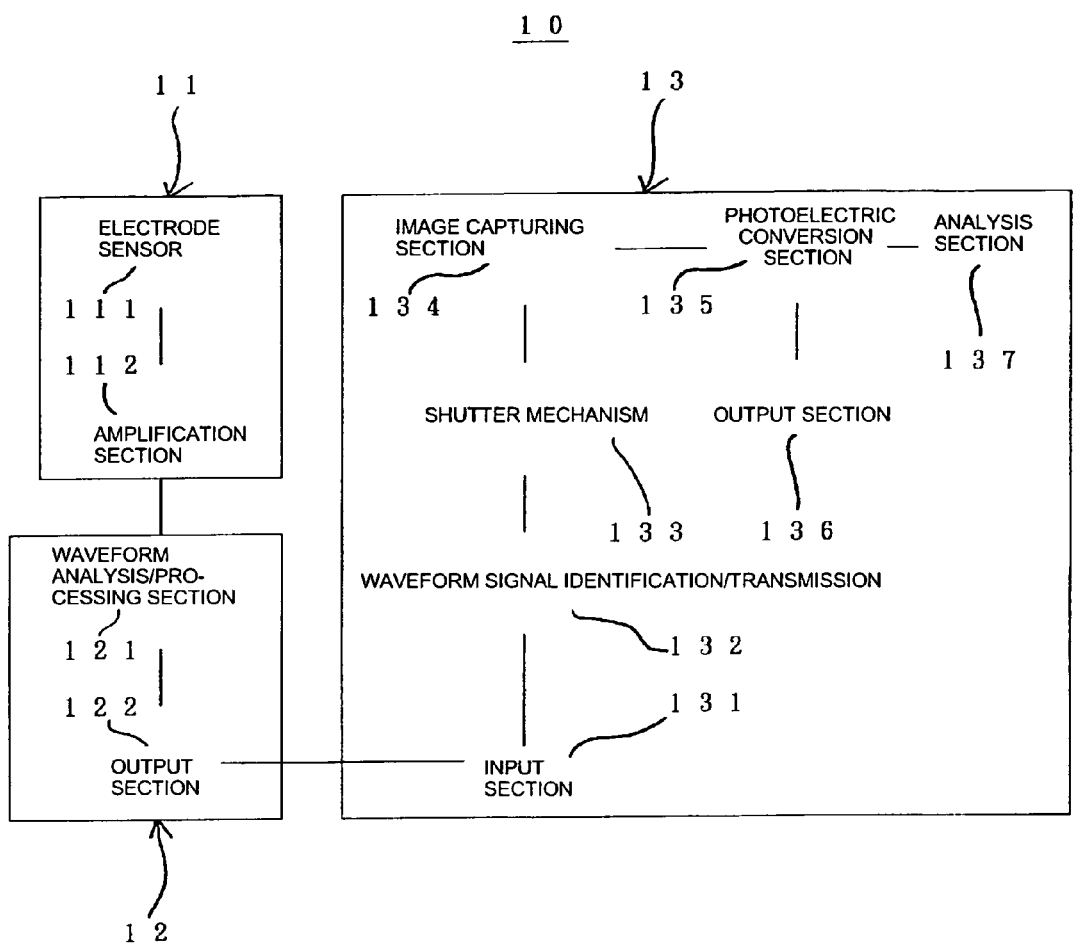
FIG. 1 is a block diagram showing the configuration of an embodiment of the eyeground image detection system.

FIG. 1 is a block diagram showing the configuration of an embodiment of the eyeground image detection system employed for implementing the present detection system.

As shown in FIG. 1, the detection system of the present invention 10 includes an electrocardiographic signal detection unit 11, an electrocardiographic signal identification unit 12, and an eyeground image detection unit 13.

The electrocardiographic signal detection unit 11 includes an electrode sensor 111 and an amplification section 112. The electrocardiographic signal identification unit 12 includes a waveform analysis/processing section 121 and an output section 122. The eyeground image detection unit 13 includes an input section 131, a waveform signal identification/transmission section 132, a shutter mechanism 133, an image capturing section 134, a photoelectric conversion section 135, an output section 136, and an analysis section 137.

The electrode sensor 111 of the electrocardiographic signal detection unit 11 contains, for example, a piezoelectric element. The electrode sensor 111 is a mechanism which is mounted on the chest or another site of a subject, to thereby detect the output electrocardiographic signal. The amplification section 112 is a mechanism for amplifying the electrocardiographic signal detected by the electrode sensor 111.

The waveform analysis/processing section 121 of the identification unit 12 is a mechanism for subjecting the electrocardiographic signal amplified by the amplification section 112 to any processing required in the present invention. For example, when a pulse wave signal of an R wave is sent to the below-described shutter mechanism 133 at a specific timing, the waveform analysis/processing section specifically selects a specific pulse wave of the R wave at a specific timing with respect to an arbitrary point of the R wave (e.g., at a certain point in time after a rising point of the R wave). The waveform analysis/processing section 121 may include selective amplification means, such as a filter amplifier, for specifically amplifying a pulse wave signal of a specific electrocardiographic signal corresponding to a specific timing. If desired, the waveform analysis/processing section 121 may include an A/D conversion mechanism for digitizing an electrocardiographic signal (an analog signal).

The output section 122 is a mechanism (e.g., an output terminal) for outputting to the eyeground image detection unit 13 an electrocardiographic signal selectively amplified in the waveform analysis/processing section 121.

The input section 131 of the eyeground image detection unit 13 is a mechanism (e.g., an input terminal) for inputting to the detection unit a selectively amplified electrocardiographic signal output from the output section 122. The waveform signal identification/transmission section 132 is a mechanism for identifying an electrocardiographic signal input by means of the input section 131, and transmitting the signal as an appropriate ON/OFF signal to the shutter mechanism 133. The shutter mechanism 133 includes means for responding to the "ON" signal of the ON/OFF signal (e.g., a pulse signal corresponding to a specific electrocardiographic signal) to thereby operate the image capturing section 134, and for responding to the "OFF" signal (e.g., a signal other than the above pulse signal) to thereby stop the operation of the image capturing section 134. Therefore, the image capturing section 134 is operated at a timing synchronized with a specific electrocardiographic signal, to thereby photograph the eyeground of a subject. If desired, the image capturing section 134 includes a mechanism employed in a typical eyeground camera for photographing the eyeground of a subject, such as an eyepiece, a light source (visible rays, appropriate ultraviolet rays, or appropriate infrared rays are available), an alignment mechanism, or a view angle adjustment mechanism.

Optical data on an eyeground image which has been captured in the image capturing section 134 synchronized with a specific electrocardiographic signal are converted to electrical data (which may be analog data or digital data) in the photoelectric conversion section 135. The resultant electrical data (e.g., a monitored image or a printed image) are output through the output section 136, and the captured eyeground image is provided to a measurer. When the electrical data are subjected to analysis in terms of eyeground vein diameter in the analysis section 137, the thus-analyzed data can be correlated with pulse wave propagation through an intracerebral blood vessel (i.e., the state of blood blow in the brain) (the present detection system 1), and the thus-analyzed data can be correlated with the state of sclerosis of a capillary artery (the present detection system 2).

The analysis section 137 includes appropriate software; for example, software including a program for selecting an appropriate target site at which the diameter of an eyeground vein is measured. Examples of software for implementing the present detection system 1 include software including a program for measuring the diameter of an eyeground vein at a target site, and for calculating the amount of change in the eyeground vein diameter; and software including a program for correlating the thus-calculated amount of change in the eyeground vein diameter with the state of pulse wave propagation through an intracerebral blood vessel (i.e., the state of blood flow in the brain). Examples of software for implementing the present detection system 2 include software including a program for measuring, at a target site, the diameter of an eyeground vein of a subject, and for forming a time-course curve (pulse wave diagram) on the basis of data on the eyeground vein diameter as obtained at different points in time (preferably, software including a program for obtaining a differential curve of a curve of the thus-formed pulse wave diagram); and software including a program for correlating the obtained profile of the pulse wave diagram with the state of sclerosis of a capillary artery of the subject [for example, 1) a program for comparing the above-formed pulse wave diagram with a pulse wave diagram corresponding to a large- or medium sized artery of a healthy human, to thereby detect the state of sclerosis of a capillary artery of the subject on the basis of the difference between these pulse wave diagrams, or 2) a program for comparing, with known data on angiosclerosis, data in relation to the positive and negative regions of the differential curves of the above-formed pulse wave diagram and a pulse wave diagram corresponding to a large- or medium sized artery of a healthy human, to thereby detect the state of sclerosis of a capillary artery of the subject on the basis of the results of analysis of the difference between these data].

As described above, in the eyeground image detection system 10, an electrocardiographic signal of a subject is detected in the electrocardiographic signal detection unit 11; the thus-detected signal is identified in the electrocardiographic signal identification unit 12 at a specific timing corresponding to a specific pulse wave (e.g., an R wave); and the eyeground image is synchronized with the resultant electrical signal at this timing. Therefore, a reliable eyeground image which is not affected by the Windkessel phenomenon can be obtained in the eyeground image detection unit 13. When data on eyeground vein diameter obtained from the reliable eyeground image are subjected to appropriate processing treatment, which is optionally performed as desired, data in relation to pulse wave propagation through an intracerebral blood vessel of the subject (i.e., data in relation to blood flow in the brain) can be obtained in the present detection system 1, whereas data in relation to sclerosis of a capillary artery of the subject can be obtained in the present detection system 2.

Figure 2:
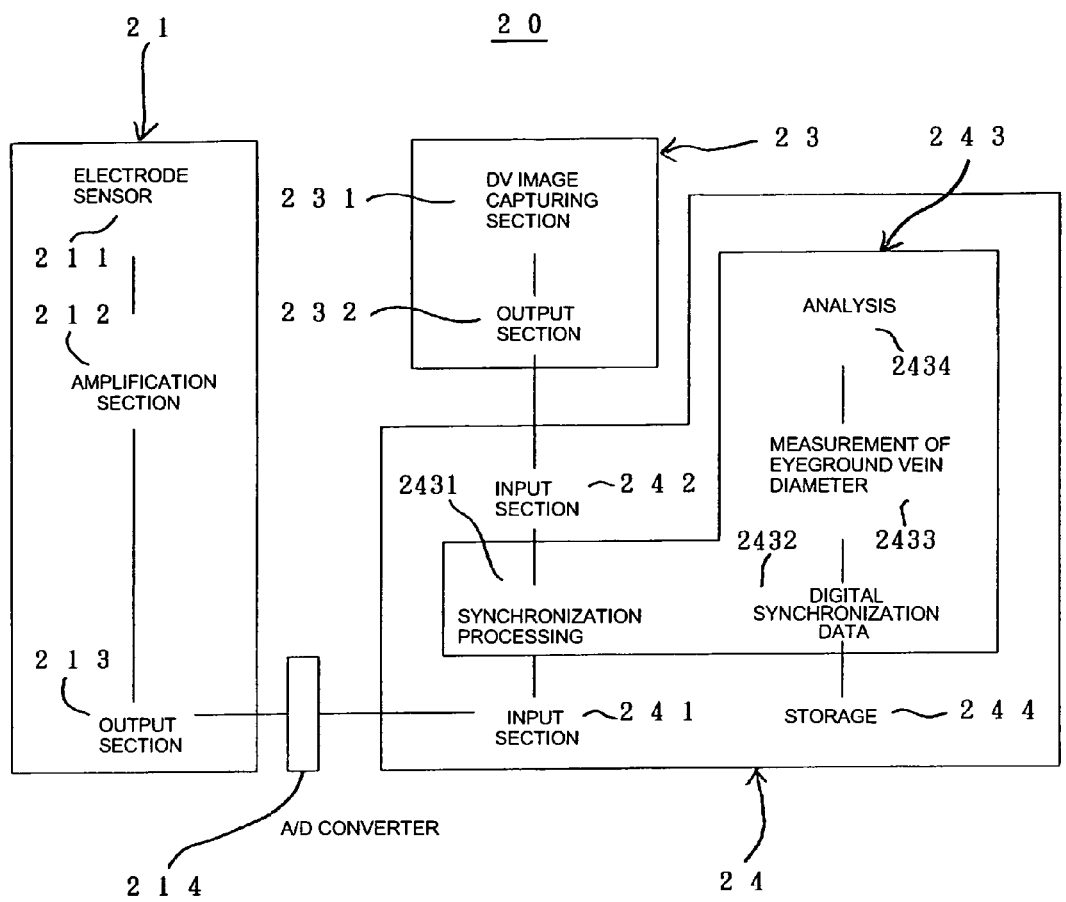
FIG. 2 is a block diagram showing the configuration of another embodiment of the eyeground image detection system.

FIG. 2 is a block diagram showing the configuration of another embodiment of the present detection system.

FIG. 2 shows the present detection system 20, which is a best mode of the present detection system, wherein a process performed in the aforementioned present detection system 10 (e.g., synchronization between an electrocardiographic signal and an eyeground image) is performed by use of a computer 24.

In the present detection system 20, since synchronization processing is performed in the computer 24, an electrocardiographic signal is transmitted from an output section 213 of an electrocardiographic signal detect-on unit 21 directly to an input section 241 of the computer 24. The electrocardiographic signal is preferably subjected to digitization processing by use of, for example, an A/D converter 214.

In an eyeground image detection unit 23, an eyeground image of a subject is captured by means of a DV image capturing section 231 (corresponding to an image capturing section of a digital video camera). A motion image signal is extracted from the resultant eyeground image, and the motion image signal is output through an output section 232, and input to the computer 24 through an input section 242 via, for example, a DV capture card. A digital video camera included in the DV image capturing section 231, which is employed for measuring a subtle change in the diameter of an eyeground vein, preferably has the highest possible resolution. Specifically, the digital video camera preferably has a resolution of 2,000,000 pixels or more. If desired, the DV image capturing section 231 includes a mechanism employed in a typical eyeground camera for photographing the eyeground of a subject, such as an eyepiece, a light source (visible rays, appropriate ultraviolet rays, or appropriate infrared rays are available), an alignment mechanism, or a view angle adjustment mechanism.

The motion eyeground image digital signal input to the computer 24 and the electrocardiographic signal input through the input section 241 are combined in parallel in a processing device 243 of the computer 24 so as to synchronize motion eyeground image data with the electrocardiographic signal in the same frame (synchronization processing 2431), thereby yielding digital synchronization data (2432) of the motion eyeground image data and the electrocardiographic signal. If desired, the synchronization data 2432 may be subjected to, for example, compression.

As described above, the synchronization data 2432 may be employed in a subsequent step (e.g., a step for measuring the diameter of an eyeground vein). Alternatively, the synchronization data may be temporarily stored in an electronic medium (244).

In an eyeground vein diameter measurement step 2433, one or more target sites at which the diameter of an eyeground vein is measured are selected on the basis of the synchronization data 2432 (preferably, one of the target sites is the optic papilla), and the diameter of an eyeground vein is measured at the thus-selected target sites. The eyeground vein diameter is measured at the target sites and at different timings. The timings may be arbitrarily determined, so long as a change in the thus-measured eyeground vein diameter can be detected (preferably, the timings are determined so as to depend on an electrocardiographic signal).

In an analysis step 2434, the change in the eyeground vein diameter is determined on the basis of data on the eyeground vein diameter as obtained at the target sites and at the above-determined timings in the eyeground vein diameter measurement step 2433, to thereby calculate the amount of change in the eyeground vein diameter on the basis of unit time depending on an electrocardiographic signal. When a point in time "ΔT," at which different image frames in which a change in the eyeground vein diameter can be clearly detected are obtained, is determined between the above timings, the amount of change in the eyeground vein diameter on the basis of unit time can be calculated. When an electrocardiographic signal at the time "ΔT" is specified, the amount of change in the eyeground vein diameter can be caused to depend on the electrocardiographic signal.

On the basis of the amount of change in the eyeground vein diameter on the basis of unit time depending on an electrocardiographic signal, which has been calculated in the analysis step 2434, pulse wave propagation through an intracerebral blood vessel of the subject can be detected. Specifically, when no change in the eyeground vein diameter is observed, no pulse wave propagation occurs in an intracerebral blood vessel; i.e., blood flow stagnates in the brain, whereas when the amount of change in the eyeground vein diameter is smaller than a predetermined standard value, pulse wave propagation is suppressed in an intracerebral blood vessel; i.e., blood flow is reduced in the brain.

In the case where the present detection system 2 is implemented, preferably, the analysis step 2434 is replaced by, for example, an analysis step for forming a time-course pulse wage diagram from data on the eyeground vein diameter as obtained at the aforementioned different timings in the eyeground vein diameter measurement step 2433. When the profile of the pulse wave diagram formed in the analysis step is correlated with the degree of progress of sclerosis of a capillary artery of the subject, to thereby determine the degree of sclerosis of the capillary artery (i.e., the degree of aging of the capillary artery) of the subject, the present detection system 2 can be implemented in an efficient manner. Specifically, when the above-formed pulse wave diagram includes an irregularly curved portion or a portion corresponding to sharp change in the eyeground vein diameter unlike the case of a pulse wave diagram corresponding to the pulsation of a large- or medium-sized artery of a healthy human, and when the change in the eyeground vein diameter is smaller as compared with the case of a healthy human having the same blood pressure as the subject, sclerosis of a capillary artery of the subject can be determined to progress. Alternatively, the state of sclerosis of the capillary artery of the subject can be determined on the basis of the difference between differential curves corresponding to the above-described pulse wave diagrams (e.g., the difference between known data on angiosclerosis and data in relation to the positive and negative regions of the differential curves).

Figure 3B:
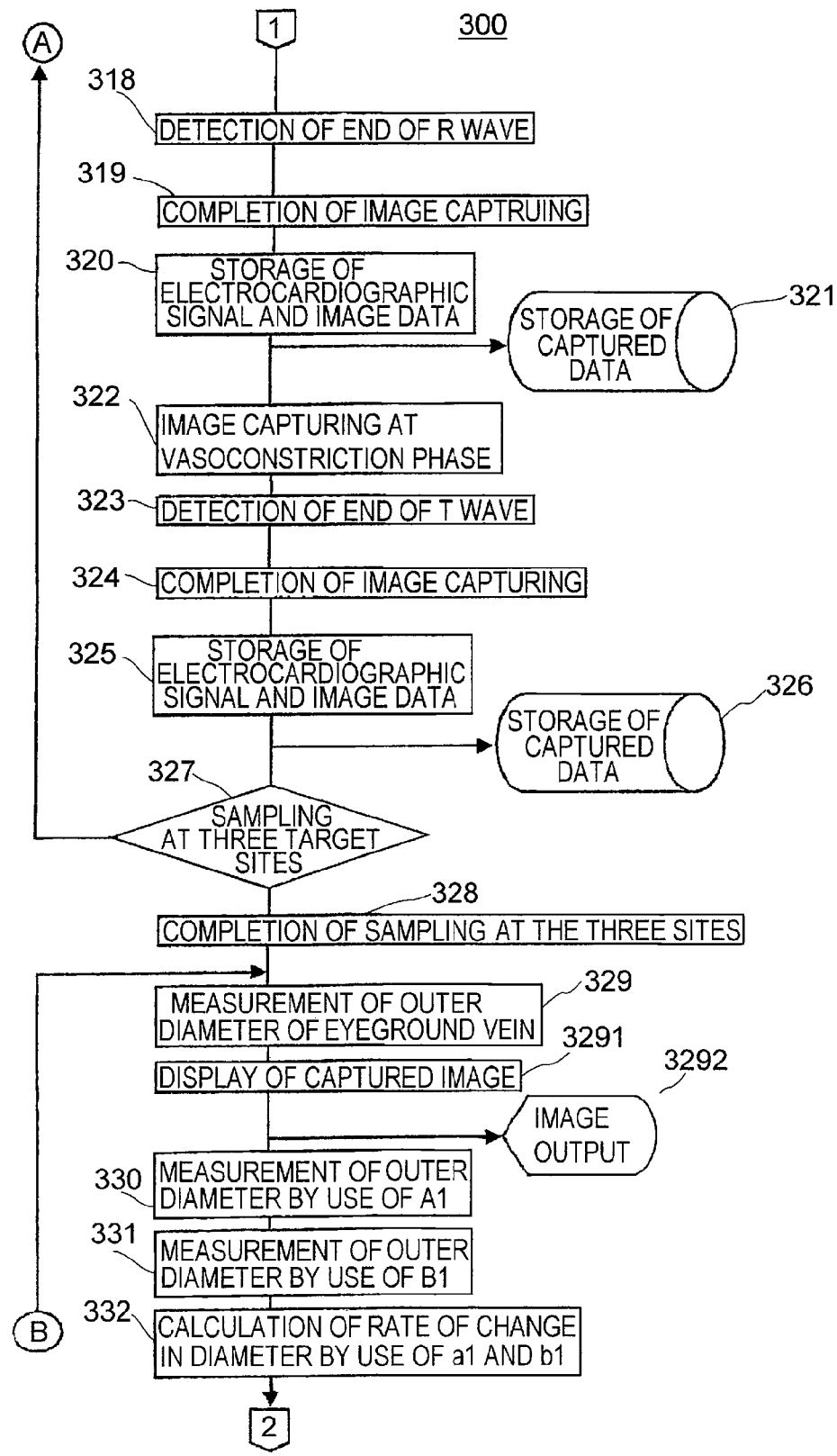
Figure 3C:
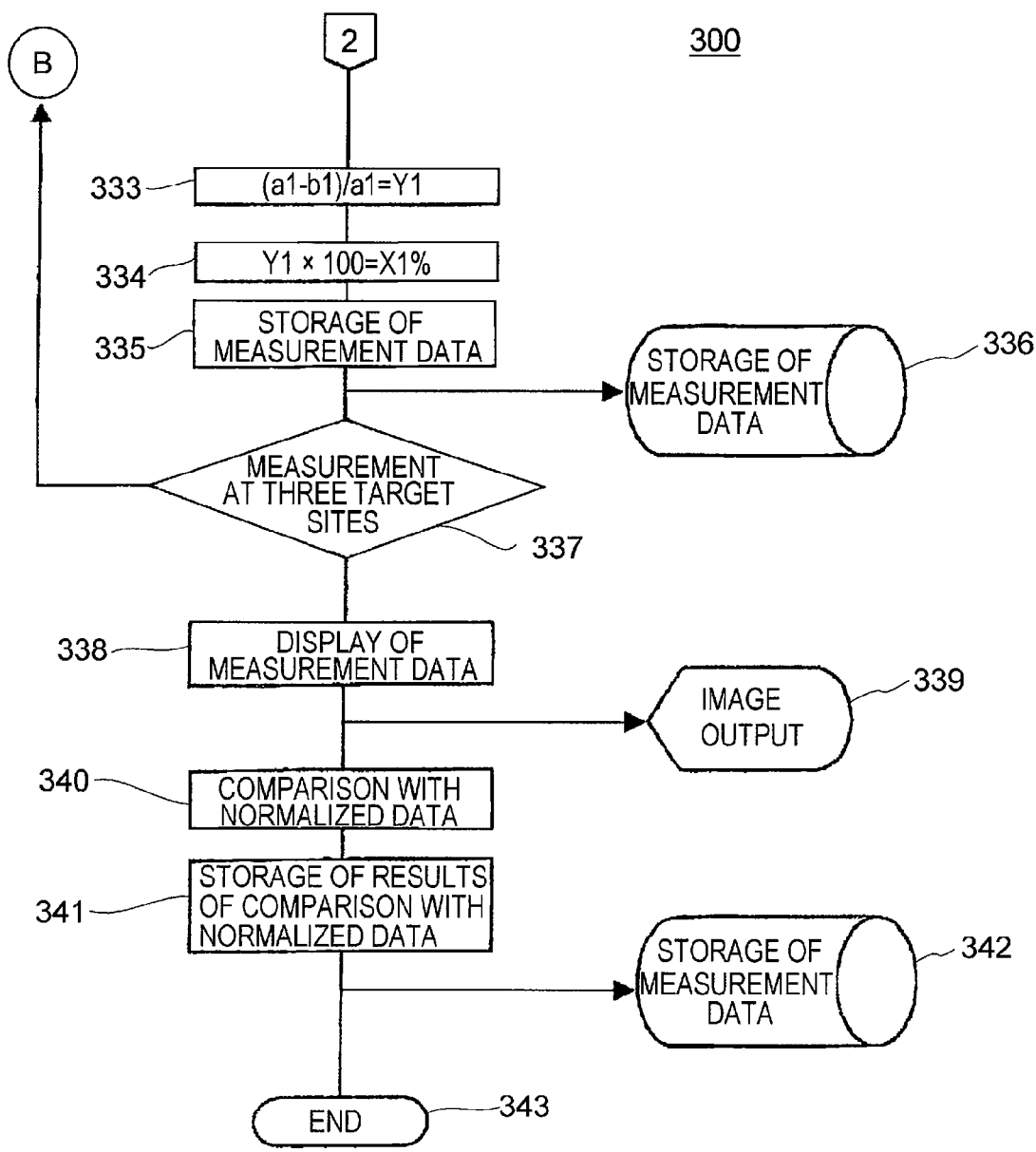

FIGS. 3A through 3C show an example of a flowchart (300) on the basis of the algorithm of the present software employed in a processing unit of the computer 24 of the present detection system 20.

As shown in FIG. 3A, in a step 301 "start," the computer 24 is set up such that the present software can execute the process shown in the flowchart 300. In a step 302 "data input," data on a subject are input. Examples of the subject data include, but are not limited to, ID No., name, age, and sex. If desired, blood pressure data may be input.

In a step 303 "electrocardiogram confirmation," whether or not an electrocardiographic signal of the subject is correctly output is confirmed, and whether or not an electrocardiogram of the subject has any abnormality is confirmed. After this confirmation step is complete, the thus-digitized electrocardiographic image is input to the computer 24 (304). In a step 305 "VTR confirmation," whether or not an eyeground image of the subject is correctly captured by a digital video camera is confirmed by means of, for example, a display of the video camera. After this confirmation step is complete, digital data on the eyeground image are input to the computer 24 (306).

In order to confirm that the input steps 304 and 306 have been performed correctly, reception of the electrocardiographic signal and the eyeground image is confirmed on a display of the computer 24 (307), and subsequently the eyeground image and an electrocardiographic image are displayed on the display (308). In the step 308 "image output," preferably, the eyeground image and the electrocardiographic image are simultaneously displayed.

In a step 309 "papilla magnification," in which a target site at which the diameter of an eyeground vein is to be measured is determined, the optic papilla is selected as the target site, and the vicinity of the optic papilla is magnified by means of a zoom-in function of the digital video camera. The thus-magnified optic papilla image can also be displayed on the display (310).

In order to precisely specify the target site, the above-magnified optic papilla image is further magnified, and eyeground veins at the target site are photographed (311). After the target site is determined, in order to combine motion eyeground image data in parallel with electrocardiographic signal data, or to obtain electrocardiographic signal data which can be combined in parallel with motion eyeground image data, electrocardiographic signals are captured for five seconds (312), and motion eyeground image data captured in synchronization with the electrocardiographic signals are stored (313).

After capturing is complete (314), the thus-stored images synchronized with the electrocardiographic signals are replayed on the display of the computer (315), stationary images are sampled at arbitrary points in time, and eyeground vein images are sampled at the periphery of the optic papilla (i.e., a target site) (316).

Next will be described a step (317) for obtaining stationary eyeground vein images at a vasodilation phase (at a constriction phase of veins) [the steps 301 through 317 are shown in FIG. 3A].

Since the end of an R wave corresponds to a vasodilation phase, an eyeground vein image is captured in synchronization with an electrocardiographic signal corresponding to the end of an R wave (318 and 319). Preferably, eyeground vein images are captured in synchronization with electrocardiographic signals corresponding to the ends of different R waves detected during the five-second measurement (in the present example, three R waves are considered to be present). Eyeground vein images (A1, A2, and A3, which are in sequential order in time) captured in synchronization with electrocardiographic signals corresponding to the ends of three R waves are stored (320 and 321).

Next will be described a step (322) for obtaining stationary eyeground vein images at a vasoconstriction phase (at a dilation phase of veins).

Since the end of a T wave corresponds to a vasoconstriction phase, an eyeground vein image is captured in synchronization with an electrocardiographic signal corresponding to the end of a T wave (323 and 324). Preferably, eyeground vein images are captured in synchronization with electrocardiographic signals corresponding to the ends of different T waves detected during the five-second measurement (in the present example, three T waves, which are detected immediately after the aforementioned three respective R waves, are considered to be present). Eyeground vein images [B1 (immediately after A1), B2 (immediately after A2), and B3 (immediately after A3), which are in sequential order in time] captured in synchronization with electrocardiographic signals corresponding to the ends of three T waves are stored (325 and 326).

In a step 327, a process including the above steps 317 through 326 is repeated at other target sites of the optic papilla (two sites: total three sites). Specifically, the first and second cycles of the process (steps 317 through 326) are performed according to a return order (A). After the third cycle of the process is performed, a step 328 is performed, and then a step 329 and subsequent steps are performed. In the present example, sampling is performed at three sites of the optic papilla. However, the number of the sampling sites may be less than three (but at least one) or more than three. The more the number of the sampling sites, the more enhanced the reliability of data. However, the more the number of the sampling sites, the longer the time required for executing the algorithm.

As described above, in the case where the present detection system 2 is implemented, when, in the above repetition process, the points in time at which A1, A2, A3, B1, B2, and B3 are captured are advanced or delayed by about 10 milliseconds; i.e., image capturing is performed at a plurality of points in time, eyeground vein diameter data corresponding to such points in time can be obtained for a variety of points in time.

Next will be described a step (329) for measuring the outer diameter of an eyeground vein. Firstly, the above-captured images are displayed through image output (3291 and 3292). Subsequently, the eyeground vein image A1—which has been captured in synchronization with the end of an R wave—and the eyeground vein image B1—which has been captured in synchronization with the end of a T wave subsequent to the R wave—are selected from among the above-captured eyeground vein images (captured images), and the outer diameter of an eyeground vein is measured by use of these selected images (the outer diameter of an eyeground vein measured by use of A1 is taken as "a1": 330, and the outer diameter of an eyeground vein measured by use of B1 is taken as "b1": 331). Next will be described a step (332) for obtaining the rate of change in the eyeground vein diameter by use of a1 and b1 [the steps 318 through 332 are shown in FIG. 3B].

Specifically, Y1 is calculated by use of the formula (a1−b1)/a1=Y1 (333), and then X1 is calculated by use of the formula Y1×100=X1 (%) (334). The thus-calculated X1 is stored (335 and 336). The calculation/data storage steps 329 through 336 are performed on a combination of the eyeground vein images A2 and B2 and a combination of the eyeground vein images A3 and B3. In a step 337, the calculation/data storage steps 329 through 336 are performed at other target sites of the optic papilla (two sites: total three sites) in a manner similar to that described above [according to a return order (B)]. The number of the cycle of the repetition process (including the calculation/data storage steps 329 through 336) is equal to that of the aforementioned sampling sites (three sites in the present example).

Thus, the rate of change in the eyeground vein diameter can be calculated by use of the software which executes the steps shown in the flowchart 300.

The thus-calculated rate of change in the eyeground vein diameter is incorporated into the data on the subject, and stored.

As described above, the eyeground vein images to be sampled may be determined arbitrarily, so long as electrocardiographic signals with which the images are to be synchronized are specifically extracted, and a change in the eyeground vein diameter can be specified when the images are compared with one another.

In the case where the present detection system 2 is implemented, when data on the eyeground vein outer diameter obtained at different points in time as described above are plotted in a time-course manner, to thereby form a pulse wave diagram, the state of sclerosis of a capillary artery can be detected on the basis of the pulse wave diagram. A differential curve corresponding to the pulse wave diagram can also be employed for detecting the state of sclerosis of a capillary artery.

The aforementioned software may include, for example, an additional function for displaying data on the above-measured eyeground vein diameter in parallel with normalized data (e.g., normalized data obtained by normalizing, with respect to age or sex, the rate of change in eyeground vein diameter), and for comparing the eyeground vein diameter data with the normalized data. Specifically, the software may include an additional function for displaying data on the above-measured eyeground vein diameter of the subject on the display of the computer 24 (338 and 339), and for comparing the eyeground vein diameter data with the normalized data (340). Specifically, the software may include an additional function for displaying the above-calculated values in parallel with the normalized data, and for calculating the deviation of the calculated values on the basis of the normalized data. The results of the above comparison can be stored as data on the subject (341 and 342).

The lower limit of blood pressure (to which blood pressure level can be reduced) of the subject can be calculated by correlating the above-calculated values with data on the blood pressure of the subject. Specifically, a standard value of the rate of change in eyeground vein diameter—which value is obtained with respect to age, etc.—is applied to the subject, thereby calculating a blood pressure value which could be secured, and the blood pressure value can be used as the lower limit of blood pressure to which blood pressure level can be reduced by use of, for example, a hypotensive drug. A program for executing means for calculating the lower limit of blood pressure may be incorporated into the present software (not illustrated). In the case where the present detection system 2 is implemented, the blood pressure of the subject can be correlated with a standard value of the range of change in eyeground vein diameter (a pulse wave diagram corresponding to the standard value is similar to that corresponding to a large- or medium-sized artery). When the range of change in the eyeground vein diameter of the subject is smaller than the standard value, this can be used, among other factors, to determine progress of sclerosis of a capillary artery of the subject.

Thus, a series of steps shown in the flowchart (300) on the basis of the algorithm of the present software is ended (343) [the steps 333 through 343 are shown in FIG. 3C].

As described above, the algorithm can be programmed by use of a typical computer programming language.

INDUSTRIAL APPLICABILITY

The present invention provides a pulse wave propagation detection system which enables monitoring the state of blood flow in the brain and the state of sclerosis of a capillary artery.

The invention claimed is:

1. A pulse wave propagation detection system comprising electrocardiographic signal detection means for detecting a first electrocardiographic signal at a first point, and for detecting a second electrocardiographic signal at a second point; and
eyeground image detection means for detecting eyeground image data in synchronization with the first time point and the second time point, and for detecting pulse wave propagation in an intracerebral blood vessel on the basis of a change in a diameter of an eyeground vein, the diameter being measured at a target site of the eyeground image data synchronized with the first electrocardiographic signal detected at the first point and the second electrocardiographic signal detected at the second point.

2. A pulse wave propagation detection system according to claim 1, wherein a state of sclerosis of a capillary artery is detected on the basis of a pulse wave diagram prepared based on the change in the diameter of the eyeground vein.

3. A pulse wave propagation detection system according to claim 2, wherein the change in the diameter of the eyeground vein is a change in the diameter of the eyeground vein at an optic papilla.

4. A pulse wave propagation detection system according to claim 2, wherein the change in the eyeground vein diameter is the difference between the diameter of an eyeground vein as measured on the basis of an eyeground image synchronized with an R wave, which is an electrocardiographic signal, and the diameter of the eyeground vein as measured on the basis of an eyeground image synchronized with a T wave, which is an electrocardiographic signal.

5. A pulse wave propagation detection system according to claim 2, wherein the eyeground image detection means detects the eyeground image data, synchronized with the first electrocardiographic signal detected at the first point and the second electrocardiographic signal detected at the second point, by extracting, on a computer display, stationary eyeground images respectively synchronized with the first electrocardiographic signal detected at the first point and the second electrocardiographic signal detected at the second point from a motion eyeground image.

6. A pulse wave propagation detection system according to claim 5, wherein the eyeground image detection means extracts the stationary eyeground images respectively synchronized with the first electrocardiographic signal detected at the first point and the second electrocardiographic signal detected at the second point while displaying the motion eyeground image and an electrocardiogram on the computer display.

7. A pulse wave propagation detection system according to claim 5, wherein the eyeground image detection means comprises executing means for calculating the change in the diameter of the eyeground vein on the basis of the eyeground image data synchronized with an arbitrary electrocardiographic signal.

8. A pulse wave propagation detection system according to claim 7, wherein the executing means correlates the change in the diameter of the eyeground vein with pulse wave propagation through an intracerebral blood vessel, thereby detecting the pulse wave propagation.

9. A pulse wave propagation detection system according to claim 7, wherein the executing means correlates the change in the diameter of the eyeground vein with sclerosis of the capillary artery, thereby detecting the state of sclerosis of the capillary artery.

10. A pulse wave propagation detection system according to claim 1, wherein the target site is an optic papilla.

11. A pulse wave propagation detection system according to claim 1, wherein the change in the eyeground vein diameter is the difference between the diameter of an eyeground vein as measured on the basis of an eyeground image synchronized with an R wave, which is an electrocardiographic signal, and the diameter of the eyeground vein as measured on the basis of an eyeground image synchronized with a T wave, which is an electrocardiographic signal.

12. A pulse wave propagation detection system according to claim 1, wherein the eyeground image detection means detects the eyeground image data, synchronized with the first electrocardiographic signal detected at the first point and the second electrocardiographic signal detected at the second point, by extracting, on a computer display, stationary eyeground images respectively synchronized with the first electrocardiographic signal detected at the first point and the second electrocardiographic signal detected at the second point from a motion eyeground image.

13. A pulse wave propagation detection system according to claim 12, wherein the eyeground image detection means extracts the stationary eyeground images respectively synchronized with the first electrocardiographic signal detected at the first point and the second electrocardiographic signal detected at the second point while displaying the motion eyeground image and an electrocardiogram on the computer display.

14. A pulse wave propagation detection system according to claim 12, wherein the eyeground image detection means comprises executing means for calculating the change in the diameter of the eyeground vein on the basis of the eyeground image data synchronized with an arbitrary electrocardiographic signal.

15. A pulse wave propagation detection system according to claim 14, wherein the executing means correlates the change in the diameter of the eyeground vein with pulse wave propagation through an intracerebral blood vessel, thereby detecting the pulse wave propagation.

16. A pulse wave propagation detection system according to claim 14, wherein the executing means correlates the change in the diameter of the eyeground vein with sclerosis of a capillary artery, thereby detecting a state of sclerosis of the capillary artery.

17. A pulse wave propagation detection system according to claim 1, wherein the change in the diameter of the eyeground vein is a difference between diameters of the eyeground vein at target sites corresponding to the first electrocardiographic signal detected at the first point and the second electrocardiographic signal detected at the second point, and when the difference is substantially recognized, presence of the pulse wave propagation in the intracerebral blood vessel is determined.

18. A pulse wave propagation detection system according to claim 1, wherein the change in the diameter of the eyeground vein is a difference between a first diameter of the eyeground vein at a first target site of the eyeground image data synchronized with an R wave of the first electrocardiographic signal and a second diameter of the eyeground vein at a second target site of the eyeground image data synchronized with a T wave of the second electrocardiographic signal, and when the difference is substantially recognized, presence of the pulse wave propagation in the intracerebral blood vessel is determined.

19. A computer readable storage medium storing a program which executes, on a computer, the pulse wave propagation detection system as recited in claim 12.

20. A computer readable storage medium storing a program which executes, on a computer, the pulse wave propagation detection system as recited in claim 5.

* * * * *